United States Patent

Fleischer et al.

(10) Patent No.: US 9,329,161 B2
(45) Date of Patent: May 3, 2016

(54) MONITORING OF THE FUNCTIONALITY OF A CONVERTER OF A BREATH ANALYSIS APPARATUS

(75) Inventors: Maximilian Fleischer, Hoehenkirchen (DE); Erhard Magori, Feldkirchen (DE); Roland Pohle, Herdweg (DE); Florian Reuter, Munich (DE)

(73) Assignee: Robert Bosch GmbH, Stuttgart (DE)

( * ) Notice: Subject to any disclaimer, the term of this patent is extended or adjusted under 35 U.S.C. 154(b) by 311 days.

(21) Appl. No.: 14/129,258

(22) PCT Filed: Jun. 27, 2012

(86) PCT No.: PCT/EP2012/062421
§ 371 (c)(1),
(2), (4) Date: Mar. 28, 2014

(87) PCT Pub. No.: WO2013/007516
PCT Pub. Date: Jan. 17, 2013

(65) Prior Publication Data

US 2014/0202232 A1    Jul. 24, 2014

(30) Foreign Application Priority Data

Jul. 8, 2011 (DE) .................. 10 2011 078 867
Aug. 10, 2011 (DE) .................. 10 2011 080 765

(51) Int. Cl.
*A61B 5/08* (2006.01)
*G01N 33/497* (2006.01)
*G01N 33/00* (2006.01)

(52) U.S. Cl.
CPC ............ *G01N 33/0009* (2013.01); *A61B 5/082* (2013.01); *G01N 33/0037* (2013.01); *G01N 33/497* (2013.01); *F01N 2550/02* (2013.01); *G01N 2033/0072* (2013.01)

(58) Field of Classification Search
CPC ........ A61B 5/082; A61B 5/083; A61B 5/097; G01N 2033/0072; G01N 33/0037; G01N 33/497; G01N 33/0009
See application file for complete search history.

(56) References Cited

U.S. PATENT DOCUMENTS 4,335,073 A * 6/1982 Sherwood ............ G01N 21/766
422/52
6,855,557 B2 * 2/2005 Kishkovich ........ G01N 33/0006
422/62

(Continued)

FOREIGN PATENT DOCUMENTS

DE    43 08 894 A1    9/1994
DE    101 21 262 A1   11/2002

(Continued)

OTHER PUBLICATIONS

European, Respiratory Society, and American Thoracic Society. "ATS/ERS recommendations for standardized procedures for the online and offline measurement of exhaled lower respiratory nitric oxide and nasal nitric oxide, 2005." American journal of respiratory and critical care medicine 171.8 (2005): 912.*

(Continued)

*Primary Examiner* — Lisa Caputo
*Assistant Examiner* — Punam Roy
(74) *Attorney, Agent, or Firm* — Maginot, Moore & Beck LLP

(57) ABSTRACT

A device for the gas analysis of a gas mixture includes a converter configured to convert a first gas component into a target gas component, a sensor system configured to detect the target gas component or another component of the gas mixture after the conversion by the converter, and an evaluating apparatus. The converter is further configured to change the concentration of a second gas component or to cause a conversion to a second target gas component. The sensor system is configured to determine the concentration of the second gas component or of the second target gas component. The evaluating apparatus is configured to determine a value for the aging of the converter on the basis of the concentration of the second gas component or of the second target gas component.

7 Claims, 2 Drawing Sheets

$$2KMnO_4 + H_2O + 3NO \rightarrow 3NO_2 + 2MnO_2 + 2KOH$$

(56) References Cited

U.S. PATENT DOCUMENTS

| | | | |
|---|---|---|---|
| 7,624,628 B2* | 12/2009 | Bartley | F01N 3/103 73/114.75 |
| 8,844,267 B2* | 9/2014 | Levijoki | F01N 3/035 60/274 |
| 2001/0019844 A1* | 9/2001 | Kishkovich | G01N 33/0006 436/106 |
| 2003/0046924 A1* | 3/2003 | Iihoshi | F01N 3/0835 60/277 |
| 2004/0000135 A1* | 1/2004 | Uchida | F01N 3/101 60/277 |
| 2004/0133116 A1 | 7/2004 | Abraham-Fuchs et al. | |
| 2010/0081955 A1* | 4/2010 | Wood, Jr. | A61B 5/097 600/532 |
| 2010/0106039 A1* | 4/2010 | Abraham-Fuchs | A61B 5/083 600/532 |
| 2010/0282245 A1* | 11/2010 | Star | G01N 27/4146 128/200.14 |
| 2011/0077544 A1* | 3/2011 | Abraham-Fuchs | A61B 5/082 600/532 |
| 2012/0065535 A1* | 3/2012 | Abraham-Fuchs | A61B 5/097 600/532 |

FOREIGN PATENT DOCUMENTS

| | | |
|---|---|---|
| DE | 10 2009 000 148 A1 | 7/2010 |
| EP | 1 384 069 B1 | 1/2004 |
| JP | 64-45913 A | 2/1989 |
| JP | 2000-221183 A | 8/2000 |
| JP | 2002-148193 A | 5/2002 |
| JP | 3113917 U | 8/2005 |
| JP | 2009-533682 A | 9/2009 |
| WO | 2010/115694 A1 | 10/2010 |

OTHER PUBLICATIONS

International Search Report corresponding to PCT Application No. PCT/EP2012/062421, mailed Sep. 19, 2012 (German and English language document) (7 pages).

Fruhberger et al.; Detection and Quantification of nitric oxide in human breath using a semiconducting oxide based chemiresistive microsensor; Sensors and Actuators B 76; 2001; pp. 226-234; Elsevier Science B.V., United States.

Kuzmych et al.; Carbon nanotube sensors for exhaled breath components; Nanotechnology 18; Aug. 22, 2007; IOP Publishing Ltd., United Kingdom (7 pages).

* cited by examiner

MONITORING OF THE FUNCTIONALITY OF A CONVERTER OF A BREATH ANALYSIS APPARATUS

This application is a 35 U.S.C. §371 National Stage Application of PCT/EP2012/062421, filed on Jun. 27, 2012, which claims the benefit of priority to Serial Nos. DE 10 2011 078 867.0, filed on Jul. 8, 2011 in Germany, and DE 10 2011 080 765.9, filed on Aug. 10, 2011 in Germany, the disclosures of which are incorporated herein by reference in their entirety.

BACKGROUND

The measurement of marker gases in human exhaled air represents a future noninvasive technique for detecting diseases and metabolic disorders. Possible applications in this case relate to screening, differential diagnosis as well as therapy optimization. Examples of this are NO detection for progress monitoring of an asthma therapy or differential diagnosis of COPD, the detection of lung tumors, TB or lung inflammation.

EP 1 384 069 discloses a breath conversion module to which the respiratory gas is delivered, before it is sent to the actual sensor unit. The purposes of this breath conversion module are, for example, to dehumidify the breath in order to avoid excessive loading of the sensor unit with moisture, as well as conversion of particular breath components. In the case of the asthma application, for example, NO is oxidized to $NO_2$. This is an example of the converter function in which an analyte gas, which can be detected only with difficulty, is converted into another gas which can be readily measured by the sensor. In other cases, interfering gases are oxidized to gases which cannot be detected by the sensor.

These converters wear out, and their lifetime is limited. It is possible to carry out replacement of the filter or converter after an estimated lifetime or number of use cycles. This method, however, is susceptible to error since exact monitoring of the intensity of use is necessary. Other errors are also possible: in order to avoid ageing during storage, the filter or converter is isolated from the ambient air by packaging before use or by valve control in the apparatus. If this is not achieved, the risk of premature ageing and false measurements of the breath analyzer arises.

SUMMARY

It is an object of the present disclosure to provide an apparatus for the gas analysis of a gas mixture, which is improved in respect of the problems described. This object is achieved by an apparatus as disclosed herein.

For the disclosure, it has been discovered that a direct measurement of the function of the converter by means of the target analytes, for example NO, is not possible since the concentration thereof is naturally unknown. An indirect measurement by means of a coupled gas conversion is therefore used.

The apparatus according to the disclosure for the gas analysis of a gas mixture comprises a gas converter for conversion of a first gas component into a target gas component, and a sensor system for detection of the target gas component or of another component of the gas mixture after the conversion by the converter. Furthermore, the converter is configured in order to modify the concentration of a second gas component or to cause conversion in a second target gas component, and the sensor system is configured in order to determine the concentration of the second gas component or of the second target gas component. Lastly, an evaluation device is provided, which is configured in order to ascertain a value of the ageing of the converter with the aid of the concentration of the second gas component or of the second target gas component.

In other words, a converter is used which converts or removes another gas occurring in respiratory air in a characteristically different concentration than in room air. Examples of this are water or $CO_2$. The conversion of this gas is then measured by an additional sensor for this gas, which is fitted behind the converter.

In this case, the concentration of this gas when the apparatus is blown into is measured. If the concentration of this second gas (the concentration of which in the exhaled air is known and is sufficiently stable) is modified to a sufficient extent, the conversion is functional, otherwise, for example, a warning message is generated.

To this end, the converter is expediently constructed in such a way that the conversion of the auxiliary gas ages in a way which is correlated with the conversion of the target gas. The two ageing behaviors may be determined by experiment, so that evaluation logic can then deduce the aging of the conversion of this target gas from the ageing of the conversion of the auxiliary gas. For the first time, therefore, self-monitoring of the breath converter is advantageously carried out.

In one refinement of the disclosure, the gas converter is configured in order to cause storage of the second gas component. In this case, the second gas component is chemically or physically bound.

Preferably, the evaluation device is configured in order to determine the value of the ageing of the gas converter from the fact that, when after the gas mixture enters, the concentration of the second gas component or of the second target gas component is greater or less than a threshold value.

In an alternative configuration, or in addition, the evaluation device is configured in order to determine the value of the ageing of the gas converter with the aid of the gradient of the second gas component or of the second target gas component to determine a threshold.

A preferred, but in no way restrictive, exemplary embodiment of the disclosure will now be described in more detail with the aid of the figures of the drawing. The features are represented in a schematized way.

DETAILED DESCRIPTION

The figures show an example of a measuring apparatus 10 for nitrogen oxide measurement in human breath—an asthma sensor.

In this case, the breath is delivered through a converter 11, and a system of valves 15, 16, 17, 19 ensures that either converted respiratory air or purified fresh air for regeneration of the sensor baseline is delivered to the sensors located in a measuring chamber 18.

Figure 2:
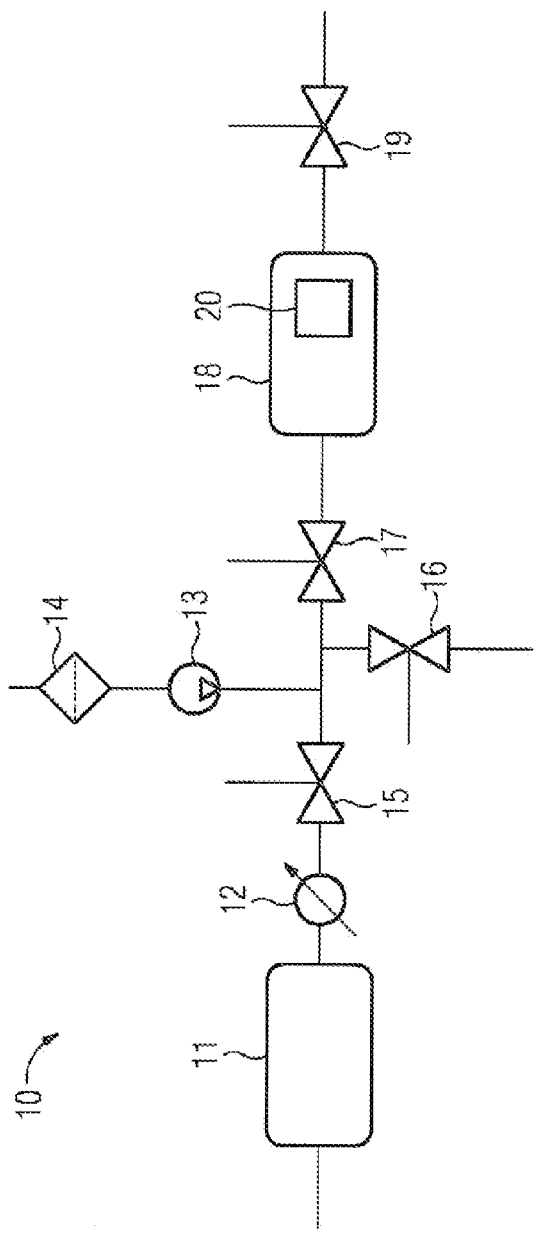
FIG. 2 shows the structure of the asthma breath analyzer.

The exemplary measuring apparatus 10 is constructed as represented in FIG. 2. Respiratory air can be delivered to the converter 11. The converter 11 is connected by a line conveying gas to a flow meter 12. This is followed by an inlet valve 15. After the inlet valve 15, there is a node of the gas line. At the node, the line conveying gas bifurcates. In a first branch, as seen from the node, a pump 13 and subsequently a filter 14 for reference air with activated carbon are provided. The first branch makes it possible to deliver purified fresh air for regeneration of the sensor baseline to the measuring chamber 18 with a sensor system 20. In a second branch, as seen from the node, an outlet valve 16 is provided. A third branch contains, as seen from the node, a second inlet valve 17, the measuring chamber 18 and a second outlet valve 19.

Figure 3:
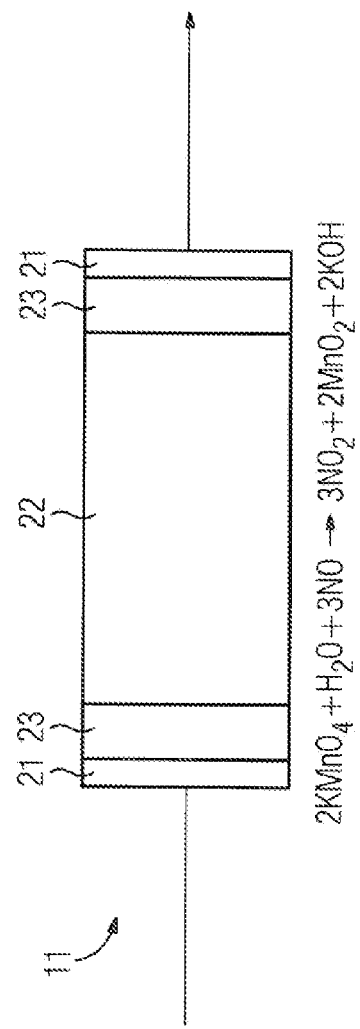
FIG. 3 shows the structure of a converter.

The converter 11 has two purposes. As represented in FIG. 3, it consists of grids 21 at both ends, between which filter elements 23 are arranged. The converter 22 is configured as a ceramic comprising potassium permanganate $KMnO_4$, or more precisely as silica gel which is partially impregnated with $KMnO_4$. The main function is conversion, caused by the $KMnO_4$, of nitrogen monoxide NO of the exhaled air into nitrogen dioxide $NO_2$ measurable by the sensor. The second function is to remove excess breath moisture using the silica gel. In the structure, there is a correlation of the ageing of the two functions.

Figure 1:
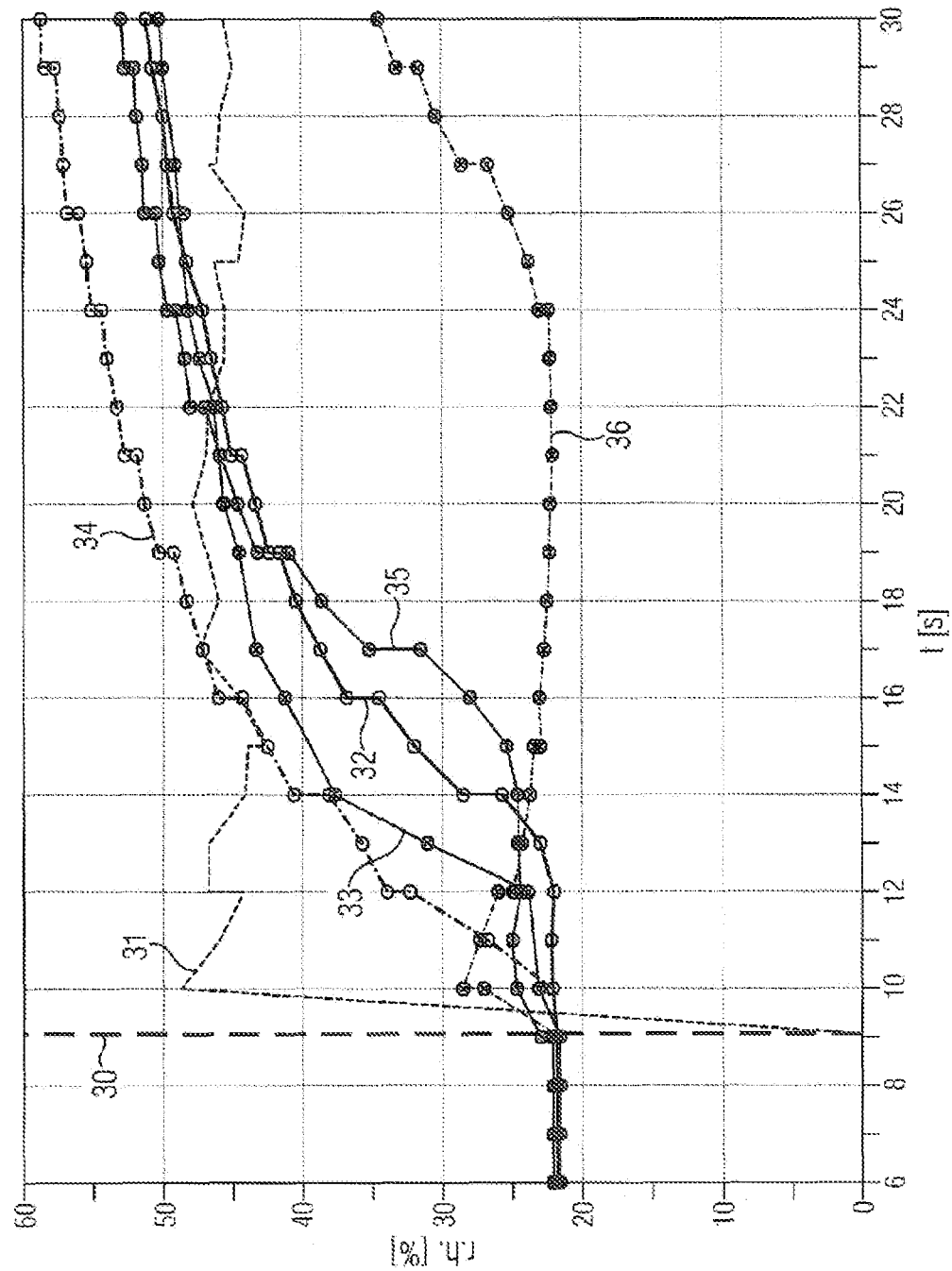
FIG. 1 shows measurement curves of sensors of an asthma breath analyzer.

FIG. 1 shows the function of indirect measurement with the aid of the relative humidity. In FIG. 1, the relative humidity after the converter 11 is plotted against time in seconds for five different samples. The relative humidity is measured by a sensor in the measuring chamber 18. At a time 30, new exhaled air with a relatively high moisture content is blown in.

A first measurement curve 36 shows the profile of the relative humidity in the case of a new converter 11. The relative humidity after the converter 11 increases almost not at all in this case. A second measurement curve 32 and a third measurement curve 35 show the profile of the relative humidity in the case of a slightly aged converter 11. In this case, the relative humidity after the converter 11 increases after a time of 8-10 seconds following the addition of the exhaled air. A fourth and a fifth measurement curve 33, 34 show the profile of the humidity after the converter 11 in the case of strongly aged converters 11. In these, the humidity increases steeply directly after the addition of the exhaled air.

From the delay with which the humidity after the converter 11 increases, and/or from the steepness of the increase, an evaluation device (not represented in FIG. 2) obtains a value of the ageing of the converter 11. In this case, it is to be noted that the actual measurement task, i.e. the measurement of NO or $NO_2$, cannot be used for this since the concentration of the NO is actually unknown, and the effectiveness of the converter therefore cannot be estimated with the aid of the measured concentration of $NO_2$. The concentration of the moisture in the exhaled air, however, is relatively well known.

Assuming ambient air having relatively low humidity, when breath is then blown into a new converter, only a slight increase in the gas humidity takes place, while the increase becomes increasingly great in the case of aged converters. The state of ageing of the converter can therefore be produced from the profile of the increase in the gas humidity. Also represented in FIG. 1 is the exhaled air pressure 31, which characterizes the blowing process.

The invention claimed is:

1. An apparatus for the gas analysis of a gas mixture, comprising:
    a converter configured (i) to convert a first gas component into a first target gas component, and (ii) to modify a concentration of a second gas component or to cause conversion in a second target gas component;
    a sensor system configured (i) to detect the first target gas component or of another component of the gas mixture after the conversion by the converter, and (ii) to determine the concentration of the second gas component or of the second target gas component; and
    an evaluation device configured to ascertain a value of the ageing of the converter with the aid of the concentration of the second gas component or of the second target gas component.

2. The apparatus as claimed in claim 1, wherein the converter carries out conversion of the second gas component into a second target gas component.

3. The apparatus as claimed in claim 1, wherein the converter is further configured to cause storage of the second gas component.

4. The apparatus as claimed in claim 1, wherein the first gas component is nitrogen monoxide and the first target gas component is nitrogen dioxide.

5. The apparatus as claimed in claim 1, wherein the evaluation device is further configured to determine the value of the ageing of the converter from the fact that, when after the gas mixture enters, the concentration of the second gas component or of the second target gas component is greater or less than a threshold value.

6. The apparatus as claimed in claim 1, wherein the evaluation device is further configured to determine the value of the ageing of the converter with the aid of a gradient of the second gas component or of the second target gas component.

7. An asthma breath analysis apparatus comprising:
    an apparatus for the gas analysis of a gas mixture, including
        a converter configured (i) to convert a first gas component into a first target gas component, and (ii) to modify a concentration of a second gas component or to cause conversion in a second target gas component,
        a sensor system configured (i) to detect the first target gas component or of another component of the gas mixture after the conversion by the converter, and (ii) to determine the concentration of the second gas component or of the second target gas component, and
        an evaluation device configured to ascertain a value of the ageing of the converter with the aid of the concentration of the second gas component or of the second target gas component.

* * * * *